United States Patent [19]

Rebell

[11] Patent Number: 4,917,104
[45] Date of Patent: Apr. 17, 1990

[54] ELECTRICALLY INSULATED "J" STIFFENER WIRE

[75] Inventor: Allan K. Rebell, North Miami, Fla.

[73] Assignee: Telectronics Pacing Systems, Inc., Englewood, Colo.

[21] Appl. No.: 205,297

[22] Filed: Jun. 10, 1988

[51] Int. Cl.⁴ .................................................. A61B 5/00
[52] U.S. Cl. .................. 128/772; 128/419 P; 128/784; 604/281
[58] Field of Search ............... 128/642, 657, 772, 784, 128/785, 786, 419 P; 604/281, 282

[56] References Cited

U.S. PATENT DOCUMENTS

| | | | |
|---|---|---|---|
| 1,060,665 | 5/1913 | Bell | 128/785 |
| 4,258,724 | 3/1981 | Balat et al. | 128/785 |
| 4,402,328 | 9/1983 | Doring | 128/785 |
| 4,454,888 | 6/1984 | Gold | 128/785 |
| 4,488,561 | 12/1984 | Doring | 128/786 |
| 4,493,329 | 1/1985 | Crawford et al. | 128/786 |
| 4,552,157 | 11/1985 | Littleford | 128/786 |
| 4,567,901 | 2/1986 | Harris | 128/786 |
| 4,586,923 | 5/1986 | Gould et al. | 604/95 |
| 4,624,265 | 11/1986 | Grassi | 128/784 |
| 4,682,596 | 7/1987 | Bales et al. | 128/303.14 |
| 4,696,667 | 9/1987 | Masch | 128/752 |
| 4,721,116 | 1/1988 | Schintgen et al. | 128/751 |

Primary Examiner—Max Hindenburg
Assistant Examiner—Randy Citrin Shay
Attorney, Agent, or Firm—Henry W. Collins; Thomas R. Vigil

[57] ABSTRACT

The cardiac lead comprises a tubular body having a proximal end and a distal end, a coiled conductor within the tubular body defining a lumen therein and having a distal end and a proximal end, a tip electrode mounted at the distal end of the tubular body, and an elongate stiffener wire comprising an elongate member made of a wire having a preset shape, a distal end and a proximal end positioned within the tubular body. The stiffener wire includes an electrical insulative material covering the elongate member for the length thereof to prevent short circuiting of the coils of the coiled conductor which may come in contact with the elongate member. A sleeve is provided for connecting a portion of the distal end of the coiled conductor to the tip electrode, and for fixing the distal end of the elongate member at the distal end of the tubular body.

20 Claims, 2 Drawing Sheets

ELECTRICALLY INSULATED "J" STIFFENER WIRE

BACKGROUND OF THE INVENTION

1. Field of the Invention

The present invention relates to a "J" shaped stiffener wire for use in a cardiac pacing lead such as a lead commonly referred to as a "J" atrial lead. More specifically, the present invention relates to a stiffener wire having a preset "J" shape, which is made of a metal material which returns to the preset shape after being deformed therefrom and which is electrically insulated so that the insulation on the stiffener wire keeps the wire from coming into contact with electrical conductors within the lead thereby to prevent establishment of a secondary electrical conductive path through the wire.

2. Description of the Prior Art

Heretofore various embodiments of curve shaped retainers have been proposed for providing pacing leads having a distal end of a preset shape. Examples of curve shaped retainers are disclosed in the following U.S. Pat. Nos.:

| U.S. Pat. No. | Patentee |
| --- | --- |
| 1,060,665 | Bell |
| 4,402,328 | Doring |
| 4,454,888 | Gold |
| 4,488,561 | Doring |
| 4,493,329 | Crawford et al. |
| 4,552,157 | Littleford |
| 4,567,901 | Harris |
| 4,586,923 | Gould et al. |
| 4,677,990 | Neubauer |

The non-analogous Bell U.S. Pat. No. 1,060,665 discloses the use of a stiffening member made of a metal, like tempered piano wire, which may be given a permanent set and which will, if bent only slightly, tend to spring back to the curved form previously given it. The wire is embedded in one wall of a prostatic catheter.

The Doring U.S. Pat. No. 4,402,328 discloses a crista terminalis atrial electrode lead which incorporates a resilient molded Silastic J shaped molding surrounding a pliant catheter and conductor for holding same in a substantial J shape.

The Gold U.S. Pat. No. 4,454,888 discloses a cardiac pacing lead with curve retainer wherein the retainer is formed from a curved flattened spring embedded within the lead body and running along a surface of a coiled conductive wire, to which the spring can be welded in one embodiment of the lead.

The Neubauer U.S. Pat. No. 4,677,990 discloses an endocardial electrode the form of which is controllable to form selected contours by exerting a tension on a freely movable tractional element extending through a channel of the electrode.

The Gould et al. U.S. Pat. No. 4,586,923 discloses a curving tip catheter which includes a wire situated within a passageway and having a distal end thereof coupled to a distal end of a flexible tip portion of the catheter. The wire extends the length of the catheter and the proximal end thereof can be pulled to deform the flexible tip portion of the catheter.

The Harris et al. U.S. Pat. No. 4,567,901 discloses a prebent ventricular/atrial cardiac pacing lead, with the prebent portion being made from a number of curved sections that interact with each other and are preferably integrally molded with each other.

The Littleford U.S. Pat. No. 4,552,157 discloses an open curve, atrial "J" electrode which incorporates direction indicating means and a plastic material having a memory in the body thereof so that, after the electrode is straightened for insertion, the electrode will return to its memorized "J" shape after the straightening element is removed with the direction indicating means defining to the user the position of the tip.

The Crawford U.S. Pat. No. 4,493,329 discloses an implantable electrode having different stiffening and curvature maintaining characteristics along its length. A "J" shaped portion of the electrode includes a spiral multifilar portion wherein the spirally wound filars are interleaved in a juxtapositional relationship to each other to provide a stiff and curved portion to the lead.

The Doring U.S. Pat. No. 4,488,561 discloses a pacing lead with insertable memory coil wherein the coil is monofilar and tends to assume a predetermined bend. The coil is provided with a lumen which receives a straightening stylet therein to aid in insertion of the lead and, once the stylet is removed, the coil returns to its predetermined bent condition.

As will be described in greater detail hereinafter, the "J" stiffener wire of the present invention comprises a noncoiled wire made of a metal material having a "memory" and including means for preventing detachment of the wire from its point of attachment to the lead at the distal end of the lead. The stiffener wire is coated with a tetrafluoroethylene or diparaxylene material to insulate the stiffener wire from the conductors of the catheter surrounding the stiffener wire. Upon flexing of the lead, such as during insertion, the stiffener wire comes into contact with the conductors of the lead, which are preferably electrically insulated, and, but for the insulative covering, could cause a secondary electrical path to form if the stiffener wire is not electrically insulated and could cut through the insulation on the conductors, causing a deviation in the resistance along the primary electrical path along the coiled conductor. The provision of an electrically insulative coating to the stiffener wire eliminates the formation of such secondary electrical pathway.

SUMMARY OF THE INVENTION

According to the invention there is provided a cardfiac lead comprising: a tubular body having a proximal end and a distal end, a coiled conductor within said tubular body defining a lumen therein and having a distal end and a proximal end, a tip electrode mounted at the distal end of said tubular body, an elongate stiffener wire comprising an elongate member made of a wire having a preset shape, a distal end and a proximal end positioned within said tubular body, an electrical insulative material covering said elongate member for the length thereof to prevent short circuiting of the coils of said coiled conductor which may come in contact with said elongate member; means for connecting a portion of the distal end of said coiled conductor to said tip electrode; and means for fixing the distal end of said elongate member at the distal end of said tubular body.

DESCRIPTION OF THE PREFERRED EMBODIMENT

Figure 1:
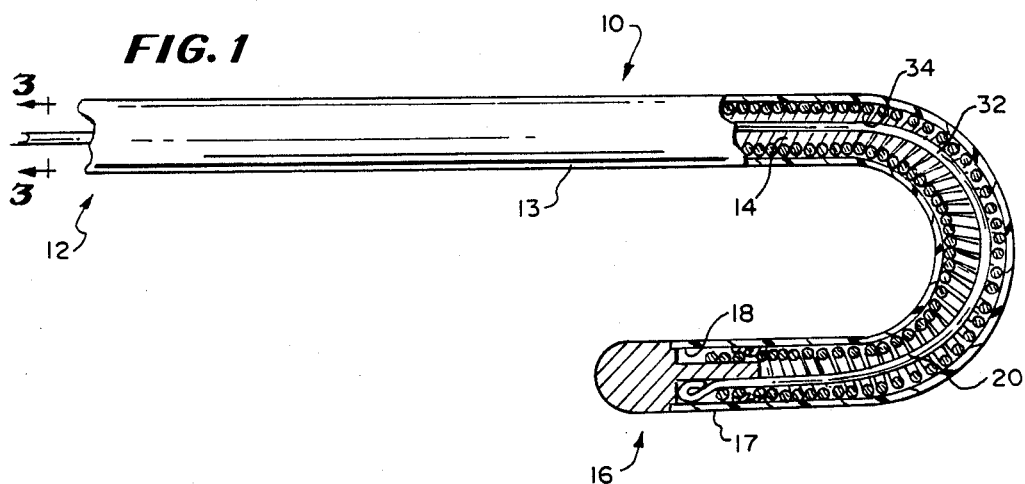
FIG. 1 is a plan view of a distal end portion of a lead body of a cardiac lead with portions broken away and shows the stiffener wire of the present invention within the lead body, formed of a catheter, with a coiled conductor of the lead forming a wall surrounding the stiffener wire.

Referring now to the drawings in greater detail, there is shown in FIG. 1 a distal section 10 of a cardiac lead 12 commonly referred to as a "J" shaped lead 12. The lead 12 includes a catheter body 13 and a coiled conductor 14 which travels the length of the catheter body 13 and is electrically connected to a tip electrode 16 mounted to a distal end portion 17 of the lead 12. A lumen 18 for the lead 12 is defined within the coiled conductor 14 and a stiffener wire 20 made in accordance with the teachings of the present invention is shown extending longitudinally within the lumen 18. The stiffener wire 20 is made of a stiff material such as stainless steel material known as MP35N or a stainless steel material known as ELGILOY T TM.

Figure 2:
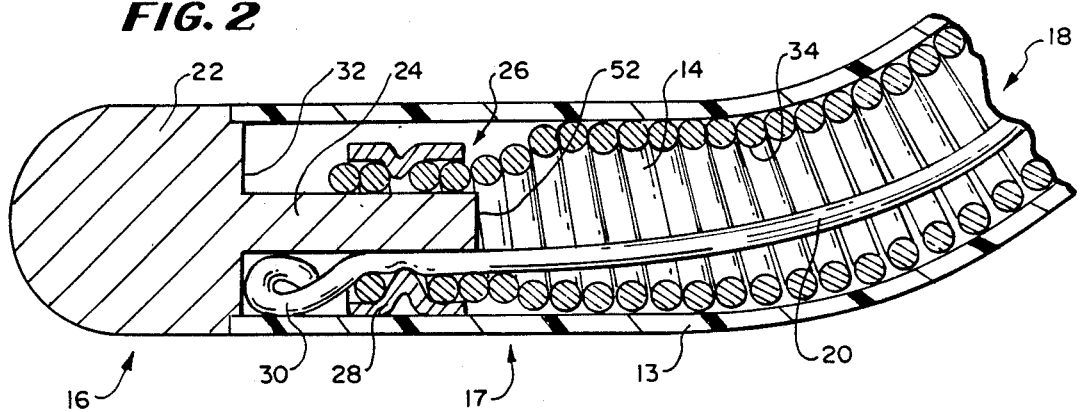
FIG. 2 is an enlarged longitudinal sectional view through a distal end portion of the lead showing one means of attachment of the stiffener wire of the present invention to the lead at a distal end of the lead.

Turning now to FIG. 2 there is shown therein an enlarged longitudinal sectional view through the distal end portion 17 of the lead 12. The tip electrode 16 has a mushroom shape and includes a head portion 22 forming the tip electrode 16 and a shank portion 24 extending inwardly into the catheter body 13.

A distal end 26 of the coiled conductor 14 extends over the shank portion 24 of the tip electrode 16 and is held in electrical engagement with the shank portion 24 by a ring or sleeve 28 crimped around the conductor distal end 26 which compresses the conductor distal end 26 against the shank portion 24 of the tip electrode 16.

The stiffener wire 20 has a curled or looped distal end 30 which extends distally past the distal end 26 of the coiled conductor 14 and into a space between the distal end 26 of the conductor 14 and a rear or proximal wall 32 of the head portion 22 of the tip electrode 16.

The stiffener wire 20 also is attached to the distal end portion 17 of the lead 12 by the crimping of the ring or sleeve 28 against the shank portion 24 of the tip electrode 16, since the stiffener wire 20 travels the length of the lead 12 along the lumen 18 inside the coiled conductor 14. The curled distal end 30 of the stiffener wire 20 is provided to keep the distal end 30 of the wire 20 from slipping through the ring or sleeve 28 and becoming disconnected from its attachment at the distal end portion 17 of the lead 12.

The stiffener wire 20, at the point of its attachment, bears against the coiled conductor 14 and against the shank portion 24 of the tip electrode 16.

Also, as illustrated in FIG. 1, numerous areas along a proximal section 32 of the stiffener wire 20 bear against the coiled conductor 14 along what can be characterized as a lumen forming wall 34 of the coiled conductor 14. Such bearing against the wall 34 of the conductor 14 during movement of the stiffener wire 20, i.e., during flexing of the stiffener wire 20 back to its preset "J" shape after removal of a straightening stylet 40, as shown in FIGS. 5-8, or during flexing of the lead could cause abrasion and breaking of any insulative coating which may be provided on the conductor 14 if the stiffener wire is uninsulated. Such a break of the insulative coating and contact with the stiffener wire 20 could form a secondary electrical current pathway within the lead 12, causing a deviation from the expected resistance along the primary electrial pathway of the coiled conductor 14. In some embodiments a coil conductor 14 may be insulated.

Figure 3:
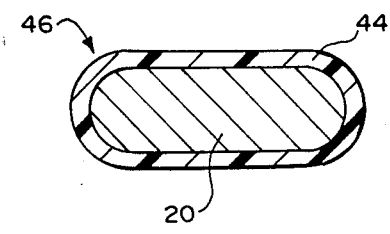
FIG. 3 is a radial cross sectional view through one embodiment of the stiffener wire of the present invention and is taken along line 3—3 of FIG. 1.
Figure 4:
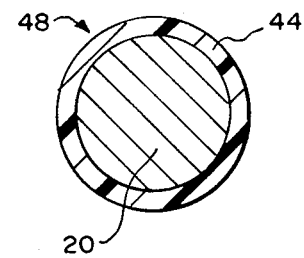
FIG. 4 is a radial cross sectional view through a second embodiment of the stiffener wire of the present invention and is taken along line 3—3 of FIG. 1.

According to the teachings of the present invention, an electrical insulative coating 44 is provided on and along the length of the stiffener wire 20, as shown in Figs. 3 and 4. In this way the possibility of formation of a secondary electrical pathway is virtually eliminated, and the resistance of the primary pathway through the conductor 14 remains constant.

Further, when the stiffener wire 20 is in the form of a "J", it has been found through empirical testing that secondary electrical pathways commonly formed by the stiffener wire 20 after flexing against the coiled conductor 14 within the lead 12, such as during flexing of the lead 12 incorporating the stiffener wire 20, are eliminated, providing a reliable electrical resistance along the primary pathway in the conductor 14 within such "J" shaped lead 12.

Turning now to FIGS. 3 and 4, two embodiments of the stiffener wire 20 are shown. The preferred embodiment 46 is shown in FIG. 3 wherein the stiffener wire 20 has a flattened oval cross sectional shape, although a round in cross section embodiment 48 of the stiffener wire 20, illustrated in FIG. 4, may also be used. In both of these embodiments 46, 48, the stiffener wire 20 is coated with a thin layer of an electrially insulative material or coating 44. These embodiments 46, 48 are shown for purposes of illustration only and should not be conidered limiting.

The electrical insulative coating 44 may be polytetrafluoroethylene or diparaxylene and need be only very thin, in the neighborhood of 0.005 and 0.0005 inch and preferably between 0.001-0.002 inch in thickness and may be applied to the stiffener wire 20 by known methods, either prior to or after "setting" the shape of the stiffener wire 20.

Figure 5:
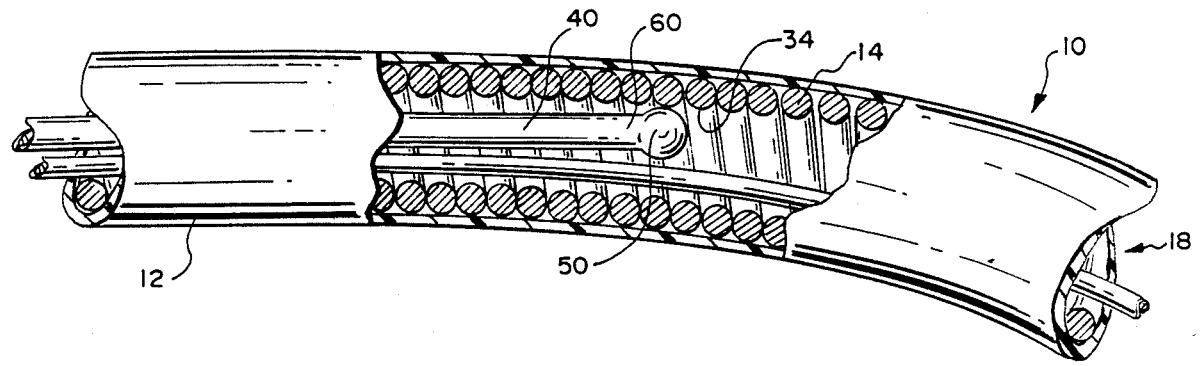
FIG. 5 is a longitudinal lateral view through a portion of the lead with portions broken away and shows a stylet being inserted within the conductor coil and alongside the stiffener wire of the lead.

Turning now to FIG. 5, the stylet 40 is shown being inserted into the lumen 18 of the lead 12 within the coiled conductor 14. This stylet 40 is inserted into a proximal end (not shown) of the lead 12 and is extended thereinto to a position where a rounded or ball tip distal end 50 of the stylet 40 is just proximal to a proximal end 52 (FIG. 2) of the shank 24 of the tip electrode 16 and is used to straighten the lead 12 from its preset "J" shape or configuration to aid the process of moving the lead 12 into and through a circulatory system to a position within a heart of a patient. Once the tip electrode 16 of the lead 12 is positioned within a chosen heart chamber, the stylet 40 is removed from within the lumen 18 of the lead 12 and the lead 12, by virtue of the preset configuration of the stiffener wire 20 therein, returns to its "J" shape.

As illustrated, the stylet 40 has a uniform diameter throughout and terminates in the ball tip 50 which is of a greater diameter than the diameter of the stylet 40. In some embodiments, a screw driver type tip maybe used which typically is smaller in lateral cross section than the stylet 4.

The stylet 40 is positioned within the lumen 18 of the lead 12 and is advanced distally within the lumen 18, where the lumen 18 deviates from a straight path, such as when it is curved in what is commonly referred to as the "J" shaped distal section 10 of the lead 12. The ball tip 50 of the stylet 40 bears against the coiled conductor 14 of the lead 12 as it abuts a far wall of the curve within the lead 12. Further, upon a greater distal advancement of the stylet 40 through the curved area, not only does the ball tip 50 of the stylet 40 bear against the coiled conductor 14, but proximal areas (not shown) of the stylet 40 also bear against the conductor 14 along the far or outer wall of the curved area of the lead 12.

Such bearing against the conductor 14 by the stylet 40 could also cause a break in any insulative coating which may be provided on the conductor 14 and, if the stiffener wire 20 comes in contact with the wire 20 in the area of a break, a secondary electrical pathway could be formed within the lead 12.

For this reason, the stylet 40 and ball tip 50 thereof are also provided with an electrically insulative coating 56 to minimize the possibility of the formation of interruptions in the insulative coating on the conductors 14.

Figure 6:
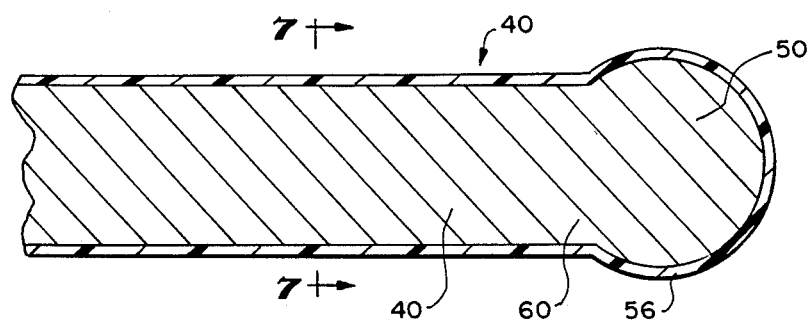
FIG. 6 is a longitudinal sectional view through the stylet of FIG. 5.
Figure 7:
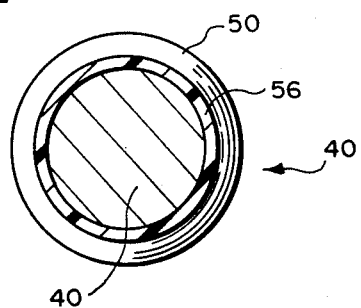
FIG. 7 is a cross sectional view through the stylet of FIGS. 5 and 6 and is taken along line 7—7 of FIG. 6.

The electrical insulative coating 56 again may be of a thin layer of polytetrafluoroethylene or diparaxylene as illustrated in FIGS. 6 and 7. The stylet 40, in cross section as shown in FIG. 7 is usually round, although this is not to be considered limiting.

The provision of a non-tapering distal end 60 to the stylet 40 provides a greater area on the stylet 40 to which the ball tip 50 can be welded.

As described above, the stiffener wire 20 has a number of advantages, some of which have been described above and other of which are inherent in the invention. Also, modifications to the stiffener wire 20 can be made without departing from the teachings of the invention. Accordingly, the scope of the invention is only to be limited as necessitated by the accompanying claims.

I claim:

1. A cardiac lead comprising:
a tubular body having a proximal end and a distal end, a coiled conductor within said tubular body defining a lumen therein and having a distal end and a proximal end, a tip electrode mounted at the distal end of said tubular body, an elongate stiffener wire comprising an elongate member made of a wire having a preset shape and having a distal end and a proximal end positioned within said tubular body, an electrical insulative material covering siad elongate member for the length thereof to prevent short circuiting of the coils of said coiled conductor which may come in contact with said elongate member; means for connecting a portion of the distal end of said coiled conductor to said tip electrode; and means for fixing the distal end of said elongate member at the distal end of said tubular body.

2. The cardiac lead of claim 1 wherein the stiffener wire is made of a deformable stainless steel material.

3. The cardiac lead of claim 2 wherein the stainless steel material is a material sold under the trademark ELGILOY.

4. The cardiac lead of claim 2 wherein the stainless steel material is a material sold under the trademark MP35N.

5. The cardiac lead of claim 1 wherein said electrical insulative material is diparaxylene.

6. The cardiac lead of claim 1 wherein said electrical insulative material is polytetrafluoroethylene.

7. The cardiac lead of claim 1 wherein the thickness of said electrical insulative material is between 0.0005 and 0.005 inch.

8. The cardiac lead of claim 7 wherein the thickness of the electrical insulative material is between 0.001 and 0.002 inch.

9. The cardiac lead of claim 1 wherein said stiffener wire is located within said lumen of said coiled conductor.

10. The cardiac lead of claim 1 wherein said stiffener wire has a curl or loop at the distal end of said stiffener wire; and said electrical insulating material covers said curled or looped distal end of said stiffener wire.

11. A cardiac lead of claim 1 wherein said stiffener wire is a "J" shaped stiffener wire and said cardiac lead is a "J" shaped cardiac lead said stiffener wire having a formed preset "J" shape and a memory for the shape, and said member is made of a deformable material, said stiffener wire has a curl or loop at the distal end of said stiffener wire; and said electrical insulative material covers said curled or looped distal end.

12. The cardiac lead of claim 1 wherein said stiffener wire includes a distal end portion and said tip electrode includes a head and a proximally extending stem and wherein said means for connecting a portion of said distal end of said coiled conductor to said tip electrode and said means for fixing the distal end of said elongate members at said distal end of the tubular body include a sleeve crimped against coils in the distal end of said coiled conductor, against said distal end portion of said stiffener wire and against said stem of said tip electrode.

13. The cardiac lead of claim 12 including a curled tip located at the distal end of said stiffener wire and positioned between said head of said tip electrode and said sleeve.

14. The cardiac lead of claim 13 wherein the curled tip is unitary with said stiffener wire.

15. A "J" shaped pacing lead comprising a tubular body having a proximal end and a distal end, a coiled conductor within said body defining a lumen therein and having a distal end and a proximal end, a tip electrode including a head and a proximally extending stem mounted at said distal end of said tubular body, a "J" shaped stiffener comprising an elongate body which has a preset formed shape and a memory for said shape, said elongate body being made of a deformable material and being positioned in said tubular body, said stiffener wire having an electrical insulating material covering the length of said stiffener, thereby to prevent short circuiting of the coils of said coiled conductor which may come in contact with said stiffener and a sleeve around and crimped against said stiffener wire, a portion of said distal end of said coiled conductor, and said stem of said tip electrode.

16. The cardiac lead of claim 15 wherein said stiffener wire is located within said lumen of said coiled conductor.

17. The cardiac lead of claim 15 wherein said distal end of said stiffener wire is curled or looped and said curl or loop is positioned between said head of said tip electrode and said sleeve.

18. A "J" shaped pacing lead comprising a tubular body having a proximal end and a distal end, a coiled conductor within said body defining a lumen therein, a tip electrode including a head and a proximally extending stem mounted at said distal end of said tubular body, and a "J" shaped stiffener wire comprising an elongate member having a distal end and a proximal end and which has a formed shape and a memory for the shape, said member being made of a deformable material, said stiffener wire being positioned in said tubular body, said stiffener wire being covered by an electrically insulative material to prevent a short circuit between adjacent coils of said coiled conductor which may come in contact with said stiffener wire, a sleeve around and crimped against said coiled conductor, said stiffener wire and said stem of said tip electrode, and a stylet for use within said pacing lead, said stylet including an elongate wire coated with an insulative material and being removably received within said lumen of said coiled conductor.

19. The stylet of claim 18 wherein said insulative material is polytetrafluoroethylene.

20. The cardiac pacing lead of claim 18 wherein said stiffener wire is located in said lumen of said coiled conductor.

* * * * *